United States Patent [19]

Deis

[11] Patent Number: 4,566,447
[45] Date of Patent: Jan. 28, 1986

[54] DROP FOOT CORRECTIVE DEVICE
[75] Inventor: Bert C. Deis, Hampton, Va.
[73] Assignee: The United States of America as represented by the Administrator of the National Aeronautics and Space Administeration, Washington, D.C.
[21] Appl. No.: 280,152
[22] Filed: Jun. 30, 1981

Related U.S. Application Data

[63] Continuation of Ser. No. 876,298, Feb. 9, 1978, abandoned.

[51] Int. Cl.[4] .................................................. A61F 3/00
[52] U.S. Cl. ................................................... 128/80 E
[58] Field of Search ............................. 128/80 E, 80 R

[56]  References Cited

U.S. PATENT DOCUMENTS 2,536,454  1/1951  McIntyre ........................... 128/80 E
3,804,085  4/1974  Eshuis et al. ....................... 128/80 E
4,102,337  7/1978  Golia ................................. 128/80 E

FOREIGN PATENT DOCUMENTS 332342   1/1921   Fed. Rep. of Germany .... 128/80 E
548527  11/1930   Fed. Rep. of Germany .... 128/80 E
523538  10/1921   France .............................. 128/80 E
593057  11/1977   Switzerland ...................... 128/80 E Primary Examiner—John D. Yasko
Attorney, Agent, or Firm—Howard J. Osborn; John R. Manning; John G. Mannix

[57]  ABSTRACT

A light-weight, economical device to alleviate a plurality of difficulties encountered in walking by a victim suffering from a drop foot condition. A legband girdles the leg below the knee and above the calf providing an anchor point for the upper end of a ligament having its lower end attached to a toe of a shoe or a toe on the foot. The ligament is of such length that the foot is supported thereby and retained in a normal position during walking.

4 Claims, 6 Drawing Figures

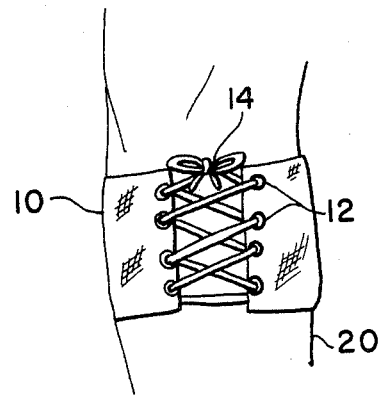
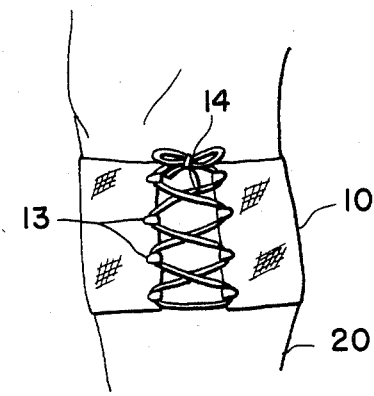
FIG. 3  FIG. 4
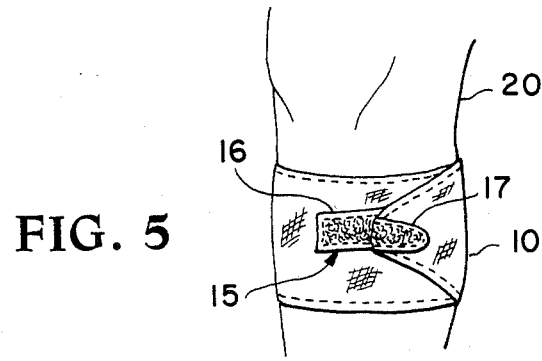
FIG. 5
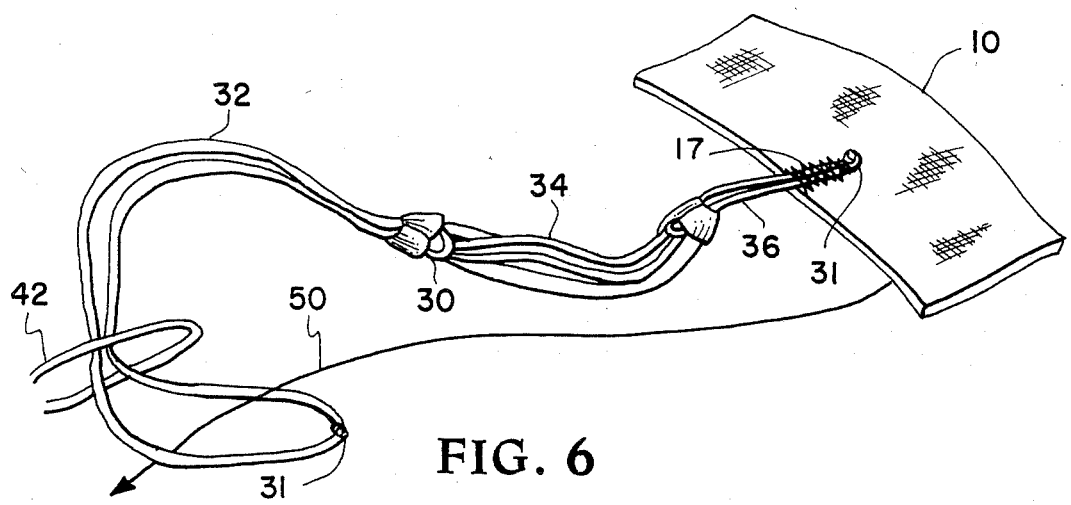
FIG. 6

DROP FOOT CORRECTIVE DEVICE

ORIGIN OF THE INVENTION

The invention described herein was made by a former Government employee and has been assigned to the United States Government and may be manufactured and used by or for the Government for governmental purposes without payment of any royalties thereon or therefore.

This is a continuation of application Ser. No. 876,298, filed Feb. 9, 1978, now abandoned.

BACKGROUND OF THE INVENTION

This invention relates to a drop foot device. More particularly, it relates to a drop foot device which utilizes a legband positionable to girdle the leg below the knee and above the calf thereof, retaining and supporting the foot with a flexible ligament affixed to and extending from a toe of the foot or the toe of a shoe worn on the foot to the legband where it is anchored.

Many people suffer a full or partial peroneal paralysis known as the "drop foot" condition which impairs their ability to walk. This condition may result from numerous diseases or afflictions. The "drop foot" condition is a term which is used to indicate the loss of the ability to control the foot with the muscles which normally operate the ankle. This condition is said to exist when the leg is lifted and the foot (which is flail) droops limply from the ankle, hence the term "drop foot." If this condition exists in a person's leg and the condition is not rectified by some external device which keeps the foot from dropping, the toe scuffs or drags along the walking surface which makes walking difficult for the victim, and can trip the victim and result in falling. This condition is normally alleviated by the application of a "short leg brace" which consists of a padded metal band that encircles the affected leg below the knee but above the calf of the victim's leg. From this metal band two vertical metal rods, one on the inner side of the leg and one on the outer side of the leg, run down to the area of the victim's ankle, where each rod is bent into a coil torsion spring to provide the flexibility and resilience required to match the ankle movements. From the coil the rods continue down outside of the shoe into the area of the arch of the shoe in front of the heel where the rods are permanently affixed to the shoe. The short leg brace is the type of remedial assistance normally provided to the victim by the makers of braces and prostehesis, and while it does alleviate the principal complaint, it has many objectionable features such as: this device is heavy, typically weighing from one-half pound to a full pound, thereby aggravating the victim's walking problem and accelerating tiring of an already weak leg; this device is quite expensive often costing $30.00 to $50.00; this device requires the wearing of a shoe and furthermore a shoe with a hard sole and a low heel; this device is not readily transferable from shoe to shoe and requires the costly services of a bracemaker if it is to be transferred; this device is quite obvious and unsightly which often causes the already sensitive victim additional embarrassment; and, this device is in general a very difficult device with which to live.

Another known device, the ankle brace, includes a strap fasteneable around the ankle having a ring and an elastic band laced through the eyelets of a shoe and tied to the ring. The ankle brace devices like the short leg braces are cumbersome and heavy. The lever arm provided by the elastic band is too short and thus inadequate to provide the desired support. This device also requires the wearing of shoes.

The present invention alleviates the problems of drop foot by providing the support needed and the flexibility required without precipitating the same difficulties as are inherent in the prior art. The present invention is inexpensive, lightweight, inconspicuous, easily transferable from shoe to shoe, and may be worn with bare feet.

An object of the present invention is a drop foot device which provides the flexibility and support to alleviate the problem of drop foot.

A further object of the invention is a drop foot device which yields the foregoing advantages and which is inexpensive.

A further object of the invention is a drop foot device which yields the foregoing advantages and which is lightweight and is not tiring to wear.

Another object of the invention is a drop foot device which yields the foregoing advantages and which is easily transferrable from shoe to shoe, detached or reattached at will.

Still another object of the invention is a drop foot device which yields the foregoing advantages and which is not obvious or unsightly.

A further object of the invention is a drop foot device which yields the foregoing advantages and which may be used with bare feet, flat heelless shoes, sneakers, crepe soled shoes, canvas shoes, and many other types of shoes.

A further object of the invention is a drop foot device which yields the foregoing advantaes and which can be fabricated and maintained in the victim's home.

A further object of the invention is a drop foot device which yields the foregoing advantages and which does not trip airport security devices.

SUMMARY OF THE INVENTION

The present invention involves a drop foot device to alleviate a plurality of difficulties encountered in walking by a victim suffering from a drop foot condition. The device includes a legband, positionable to girdle the afflicted leg of the victim below the knee and above the calf. A ligament having an upper end fixable to the legband at the anterior side of the leg and having a lower end fixable at the anterior portion of the foot provides the flexibility and support to retain the foot in a natural position during walking.

A BRIEF DESCRIPTION OF THE DRAWINGS

FIG. 3 is a side view of the victim's leg showing a lace arrangement utilizing holes;

FIG. 4 is a side view like FIG. 3 showing a lace arrangement utilizing hooks;

FIG. 5 is a side view like FIG. 3 showing a Velcro Strip legband tightness adjusting means; and FIG. 6 is a perspective view showing the details of the ligament.

DESCRIPTION OF THE PREFERRED EMBODIMENT

Figure 1:
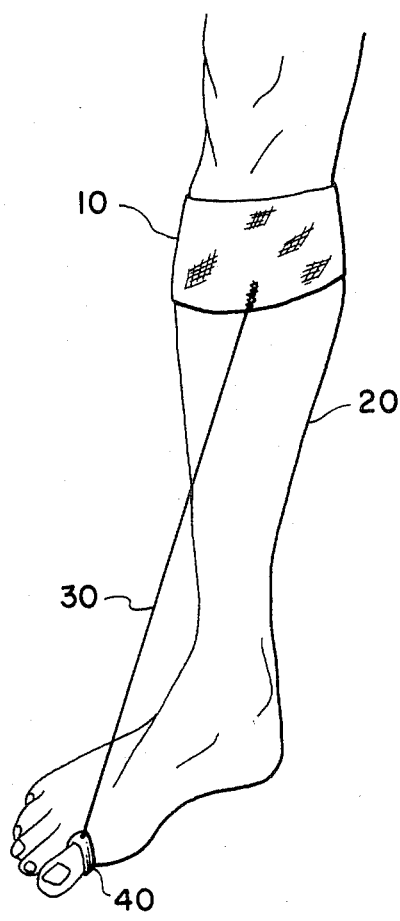
FIG. 1 is a perspective view showing the drop foot device in position on the bare foot leg of a victim.

FIG. 1 shows the preferred embodiment of the invention in position on the barefoot leg of a victim of drop foot syndrome. Legband 10 girdles leg 20 above the calf and below the knee. Legband 10 is adjusted tight enough to provide an anchor point for ligament 30 but not tight enough to impair blood circulation in the leg. A ligament, generally referred to by the numeral 30, extends from legband 10 to the foot. The upper end of ligament 30 is sewn onto or attached by some other conventional fastening means to the lower edge of legband 10 at the front of leg 20.

The lower end of ligament 30 is affixed to a toe sling 40 through which a toe of the victim may be inserted. For purposes of illustration the big toe is shown in the toe sling 40 in FIG. 1. The length of ligament 30 is such that when the victim is walking the foot is retained at an attitude which precludes dragging and scuffing on the walking surface.

Figure 2:
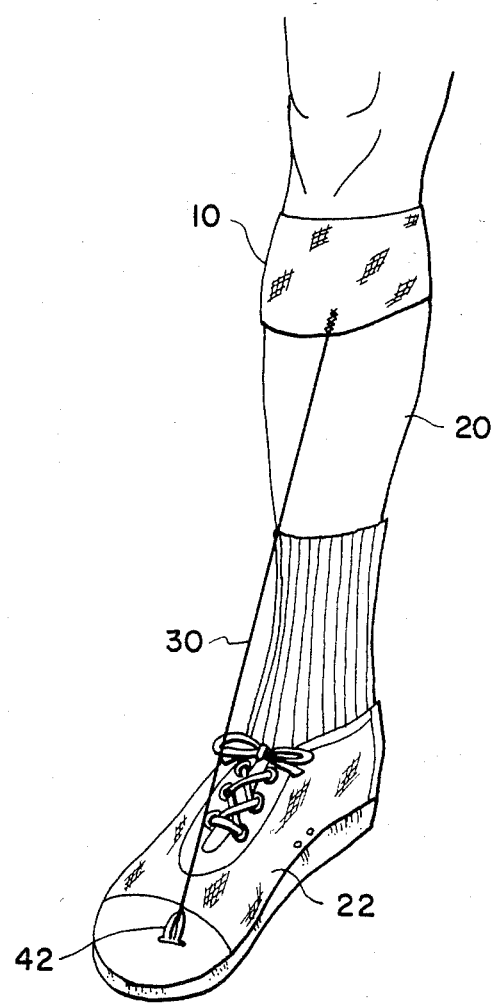
FIG. 2 is a perspective view like FIG. 1 showing the device attached to a shoe.

FIG. 2 shows the device positioned on a victim wearing a shoe 22. The device may be used with any type of shoe; a canvas sneaker is shown in the preferred embodiment for purposes of illustration. A simple modification is made to a shoe 22 to be used with the device: a loop 42, approximately 1 inch long, of monofilament nylon-type line is sewn into the toe of the shoe 22. The lower end of ligament 30 is tied by conventional means to loop 42. Since ligament 30 is easily and quickly tied and untied to loop 42, the device may be used with any number of shoes so modified.

Referring to FIG. 3, tightness adjusting means consists of a lace 14 laced through lace holes 12 in the ends of legband 10. Lace 14 is pulled to bring the ends of legband 10 together and is tied in a conventional manner. FIG. 4 shows another lace arrangement similar to the arrangement in FIG. 3 except hooks 13 are used in place of holes 12.

Refer now to FIG. 5, an alternative arrangement is shown to adjust tightness of the legband 10. A Velcro Strip generally referred to by the numeral 15 is sewn between the overlapping ends of legband 10. A Velcro Strip includes two corresponding pieces of material: one being a nylon carpet pile, the other being an array of nylon hooks. When pressed together the nylon hooks hook into the carpet pile and some degree of force is required to bend the nylon hooks in order to pull the two pieces of material apart. In the preferred embodiment the pile strip 16 is sewn to the inner overlapping end of legband 10 and the hook strip is sewn to the outer overlapping end of legband 10. The Velcro Strip allows a continuous tightness adjustment of legband 10 about leg 20.

Referring now to FIG. 6 which shows more detail of ligament 30. Ligament 30 of the preferred embodiment includes two lengths of monofilament nylon-type line 32 and 36 and a rubber band 34 or some other type of resilient or elastic material. Each of the lines 32 and 36 are looped and have their ends tied and melted together to form permanent knots 31. The rubber band 34 is tied between lower line 32 and upper line 36 to form ligament 30. The knotted end of upper line 36 is sewn to legband 10 with stitches 17 just below knot 31. The knotted end of lower line 32 is affixed to loop 42 of the preferred embodiment by inserting lower line 32 through loop 42 and pulling the whole device through lower line 32, as shown by arrow 50 in FIG. 6, and pulling tight.

The above-described ligament 30 utilizes monofilament nylon-type line and a rubber band. The use of these materials in the preferred embodiment is not intended to limit the present invention thereto, and any suitable material may be used alternatively.

The above-described description and drawings are only illustrative of one embodiment which achieves the objects, features and advantages of the present invention, and it is not intended that the present invention be limited thereto. All modifications of the present invention which come within the spirit and scope of the following claims are considered part of the present invention.

What is claimed is:

1. An apparatus for assisting a person having a foot-drop type disability, comprising;
    a leg attachment member;
    an elastomeric support strap secured to said leg attachment member; and
    a shoe with a cooperating means for attaching said support strap to said shoe, said means for attaching further comprising a loop, said loop being secured to said shoe of the wearer at a point generally on the forward portion of said shoe and on the lateral side of said shoe, while the other end of said loop is secured to said elastomeric support strap which, in turn, is secured to said leg attachment means at a point on the lateral side of the wearer's leg so that when said apparatus is worn said strap contracts to raise the wearer's foot during the time said wearer is not forcibly extending said strap by the downward extension of said foot and simultaneously effects eversion when said strap operates to raise said foot.

2. An apparatus as described in claim 1, wherein said leg attachment member comprises an adjustable band securable to the leg at a point on the lower leg on or immediately above the calf.

3. An apparatus as described in claim 2 wherein said adjustable band comprises a width of fabric; and
    an adjustable closure device affixed to said width of fabric and cooperating therewith so that either side of said band is selectively adjustable to conform to the wearer's leg.

4. An apparatus as described in claim 3, wherein said adjustable closure device comprise lengths of adhesive cloth attached to said adjustable band and said strips so that said lengths adhere cooperatively to hold said band on the wearer's leg.

* * * * *